(12) United States Patent
Fereidouni et al.

(10) Patent No.: US 12,019,250 B2
(45) Date of Patent: Jun. 25, 2024

(54) WHITE DWARF: CROSS-POLARIZED WHITE LIGHT SLIDE-FREE IMAGING

(71) Applicant: The Regents of the University of California, Oakland, CA (US)

(72) Inventors: Farzad Fereidouni, Sacramento, CA (US); Richard M. Levenson, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 296 days.

(21) Appl. No.: 17/339,092

(22) Filed: Jun. 4, 2021

(65) Prior Publication Data

US 2021/0382318 A1 Dec. 9, 2021

Related U.S. Application Data

(60) Provisional application No. 63/036,146, filed on Jun. 8, 2020.

(51) Int. Cl.
*G02B 27/28* (2006.01)
*A61B 5/00* (2006.01)
(Continued)

(52) U.S. Cl.
CPC .......... *G02B 27/283* (2013.01); *A61B 5/0071* (2013.01); *G01N 21/27* (2013.01);
(Continued)

(58) Field of Classification Search
CPC .............. G02B 27/283; G02B 21/0092; G02B 21/082; G02B 21/16; A61B 5/0071;
(Continued)

(56) References Cited

U.S. PATENT DOCUMENTS 10,582,841 B2 * 3/2020 Kang .................. A61B 1/07
2005/0141843 A1 * 6/2005 Warden .................. G01N 15/14
385/129
(Continued)

FOREIGN PATENT DOCUMENTS

EP 1002253 B1 * 2/2008 ........... A61B 5/0059
WO WO-0027276 A1 * 5/2000 ........... A61B 5/0059
(Continued)

OTHER PUBLICATIONS

Elfer KN, Sholl AB, Wang M, Tulman DB, Mandava SH, Lee BR, et al. (2016) "DRAQ5 and Eosin ('D&E') as an Analog to Hematoxylin and Eosin for Rapid Fluorescence Histology of Fresh Tissues" (Year: 2016).*

*Primary Examiner* — Michelle M Iacoletti
*Assistant Examiner* — Noah J. Haney
(74) *Attorney, Agent, or Firm* — Park, Vaughan, Fleming & Dowler LLP (57) ABSTRACT

The system includes: a sample holder configured to hold a stained tissue sample; an objective positioned to gather and focus light from the stained tissue sample; and a white light source that produces unpolarized white light and a polarizing beam splitter that allows one polarization direction of the white light to pass through to form an illumination beam having a first polarization direction, which is directed through the objective and onto the stained tissue sample causing the stained tissue sample to remit light that passes back through the objective and into the polarizing beam splitter. The polarizing beam splitter divides the remitted light into two orthogonally polarized remitted light beams, wherein one of the beams provides an imaging beam, which has a second polarization direction that is substantially orthogonal to the first polarization direction. Finally, the
(Continued)

system includes an imaging device, which captures the imaging beam.

22 Claims, 6 Drawing Sheets

(51) Int. Cl.
*G01N 21/27* (2006.01)
*G01N 21/47* (2006.01)
*G01N 21/64* (2006.01)
*G02B 21/00* (2006.01)
*G02B 21/08* (2006.01)
*G02B 21/16* (2006.01)
*G06T 7/00* (2017.01)

(52) U.S. Cl.
CPC ......... *G01N 21/47* (2013.01); *G01N 21/6486* (2013.01); *G02B 21/082* (2013.01); *G02B 21/16* (2013.01); *G06T 7/0012* (2013.01); *G01N 21/6458* (2013.01); *G02B 21/0092* (2013.01); *G06T 2207/30024* (2013.01); *G06T 2207/30096* (2013.01)

(58) Field of Classification Search
CPC ............... G01N 21/6486; G01N 21/27; G01N 21/6458; G06T 7/0012; G06T 2207/30024; G06T 2207/30096
USPC ......................................................... 356/364
See application file for complete search history.

(56) References Cited

U.S. PATENT DOCUMENTS

| | | |
|---|---|---|
| 2007/0043341 A1 | 2/2007 | Anderson et al. |
| 2007/0146634 A1* | 6/2007 | LeBlanc ................ A61B 3/156 351/221 |
| 2007/0160279 A1* | 7/2007 | Demos ................ A61B 5/0071 359/368 |
| 2008/0074644 A1 | 3/2008 | Levenson et al. |
| 2011/0116694 A1* | 5/2011 | Gareau ............. G02B 21/0076 359/383 |
| 2012/0108982 A1 | 5/2012 | Hoyt et al. |
| 2013/0242311 A1* | 9/2013 | Usami ................. G01B 9/0209 356/492 |
| 2015/0164327 A1* | 6/2015 | Yaroslavsky ........... G01N 21/21 600/407 |
| 2016/0041100 A1* | 2/2016 | Mizoguchi ......... G01N 21/6486 549/33 |
| 2016/0062098 A1* | 3/2016 | Brown .............. G02B 21/0076 600/431 |
| 2018/0172970 A1* | 6/2018 | Themelis ............... A61B 3/158 |
| 2018/0347960 A1* | 12/2018 | Tsai ....................... G02B 21/14 |
| 2019/0004299 A1* | 1/2019 | Kukura ................... G02B 21/26 |
| 2020/0150042 A1 | 5/2020 | Fereidouni et al. |
| 2021/0404917 A1* | 12/2021 | Mayerich ................. G01N 1/36 |

FOREIGN PATENT DOCUMENTS

| | | | |
|---|---|---|---|
| WO | WO-03067229 A1 * | 8/2003 | ........... A61B 5/0059 |
| WO | WO-2015134847 A1 * | 9/2015 | ........ G01B 9/02011 |
| WO | WO-2016090356 A1 * | 6/2016 | .......... H01J 49/0004 |
| WO | WO-2018204712 A1 * | 11/2018 | ............... B01L 9/52 |
| WO | 201920973 A1 | 10/2019 | |
| WO | 2020006129 A1 | 1/2020 | |

* cited by examiner

WHITE DWARF: CROSS-POLARIZED WHITE LIGHT SLIDE-FREE IMAGING

RELATED APPLICATION

This application claims priority under 35 U.S.C. § 119 to U.S. Provisional Application No. 63/036,146, entitled "White Dwarf: Cross-Polarized White Light Slide-Free Imaging" by inventors Farzad Fereidouni and Richard M. Levenson, filed on 8 Jun. 2020, the contents of which are incorporated by reference herein.

BACKGROUND

Field

The disclosed embodiments generally relate to techniques for imaging tissue samples. More specifically, the disclosed embodiments relate to a technique for imaging tissue samples that facilitates cross-polarized, white light, slide-free imaging.

Related Art

At present, conventional histopathology provides the most practical and logistically feasible technique for handling, preserving, and evaluating tumors, and for many years has been the mainstay and gold standard for cancer diagnosis. These conventional histopathology techniques typically involve formalin-fixed, paraffin-embedded (FFPE) tissue processing with microtome sectioning and staining.

Histopathology is still the definitive diagnostic tool for tissue-centered diseases. Standard histology relies on using a microtome to physically section either frozen or formalin-fixed, paraffin-embedded (FFPE) specimens into thin slices (typically 4-6 µm) prior to staining and viewing on a standard brightfield microscope. Frozen sections, while taking only 5-10 minutes to prepare, require skilled handling, and frequently do not provide diagnostic-quality slides.

Although FFPE processes can generate excellent histology, they are typically time-consuming, requiring hours or even days depending on workflow and accessibility of histology laboratories. The long processing times make these FFPE-based techniques less practical in surgical-guidance settings, wherein it is advantageous to obtain results right away, to inform a surgeon about whether they successfully removed a tumor and/or identify the type of tumor. Also, in biopsy situations, if an answer can be obtained the same day, time-critical care can be dramatically accelerated.

Hence, what is needed is a technique for imaging tissue samples without the above-described disadvantages of conventional histopathology techniques.

SUMMARY

The disclosed embodiments provide a system that images a tissue sample. This system includes: a sample holder configured to hold a stained tissue sample and an objective positioned to gather and focus light from the stained tissue sample. The system also includes a white light source that produces unpolarized white light and a polarizing beam splitter. During operation, the polarizing beam splitter receives the unpolarized white light and allows one polarization direction to pass through to form an illumination beam having a first polarization direction. The polarizing beam splitter is positioned so that the illumination beam is directed through the objective and onto the stained tissue sample, which causes the stained tissue sample to remit light that passes back through the objective and into the polarizing beam splitter. The polarizing beam splitter then divides the remitted light into two orthogonally polarized remitted light beams, wherein one of the polarized remitted light beams provides an imaging beam, which has a second polarization direction that is substantially orthogonal to the first polarization direction. Finally, the system includes an imaging device, which captures the imaging beam.

In some embodiments, the system also includes an input polarizer located between the white light source and the polarizing beam splitter, wherein the input polarizer has a polarization direction, which is substantially equivalent to the first polarization direction.

In some embodiments, the system additionally includes an output polarizer located between the polarizing beam splitter and the imaging device, wherein the output polarizer has a polarization direction, which is substantially equivalent to the second polarization direction.

In some embodiments, the imaging device includes one of the following: an eyepiece; a camera; and a digital image-capture device.

In some embodiments, the stained tissue sample is stained with an absorbing stain.

In some embodiments, the stained tissue sample is stained with hematoxylin.

In some embodiments, the stained tissue is stained with one or more of the following: eosin, rhodamine, saffron, celestine blue, and propidium iodide.

In some embodiments, the sample holder comprises an XYZ stage.

In some embodiments, the system is combined with an epifluorescence microscopy system to provide additional information in resulting images.

In some embodiments, digital images that are captured by the imaging device are computationally processed to facilitate one or more of the following: image enhancement, denoising, computational superresolution, color-mapping and machine-learning based image-processing.

The disclosed embodiments provide another system that images a tissue sample. This system includes: a sample holder configured to hold a stained tissue sample; an objective positioned to gather and focus light from the stained tissue sample, and a white light source that produces unpolarized white light. The system also includes an optical system that directs the unpolarized white light to the stained tissue sample at an oblique angle relative to an imaging path between the stained tissue sample and the objective to produce oblique illumination. The oblique illumination causes the stained tissue sample to remit light that passes through the objective to form an imaging beam. (Note that this oblique geometry helps avoid specular reflections.) Finally, the system includes an imaging device positioned to receive the imaging beam.

In some embodiments, the optical system comprises a beam splitter and a pair of axicons, which convert the unpolarized white light into a hollow cylindrical beam that passes through the beam splitter and into the objective. The objective converts the hollow cylindrical beam into a hollow conical beam, which radially converges on the stained tissue sample to produce oblique illumination, which causes the stained tissue sample to remit light that passes back through the objective and into the beam splitter. The beam splitter then reflects a percentage of the remitted light in a perpendicular direction to form the imaging beam. (Note that this beam splitter can either be an intensity beam splitter or a polarizing beam splitter.)

The disclosed embodiments provide yet another system that images a tissue sample through side illumination. This system includes a waveguide, wherein a stained tissue sample is placed against or in proximity to a surface of the waveguide. It also includes a white light source that launches white light into an input end of the waveguide to provide the side illumination, wherein a launch angle for components of the white light is greater than a critical angle between the waveguide material and air, so that the white light propagates through the waveguide via total internal reflection to reach the stained tissue sample. The launch angle is also less than a critical angle between the waveguide material and the stained tissue sample, so that when the white light reaches the stained tissue sample, the white light escapes the waveguide through refraction to illuminate the stained tissue sample. The system also includes an imaging system located on an opposite side of the waveguide from the stained tissue sample, which captures an image of the illuminated stained tissue.

In some embodiments, the white light source comprises an array of white LEDs and a lens, wherein the lens focuses light from the array of white LEDs into the input end of the waveguide.

The disclosed embodiments provide another system that images a tissue sample. This system includes: a sample holder configured to hold a stained tissue sample; a white light source that produces unpolarized white light; and an input polarizer that polarizes the unpolarized white light from the white light source to form an illumination beam, wherein the input polarizer has a first polarization direction. The system also includes an objective positioned to gather and focus light from the stained tissue sample. The system is configured so that the illumination beam hits the stained tissue sample at an oblique angle relative to an imaging path between the stained tissue sample and the objective to produce oblique illumination, wherein the oblique illumination causes the stained tissue sample to produce remitted light that passes through the objective to form an imaging beam. The system also includes an imaging device positioned to receive the imaging beam.

In some embodiments, the system also includes an output polarizer located between the objective and the imaging device, wherein the output polarizer has a second polarization direction, which is substantially orthogonal to the first polarization direction.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Overview

The disclosed embodiments provide a system called "white dwarf," which facilitates rapid imaging of thick tissue specimens via the absorption properties of a histologic dye, such as hematoxylin. Hematoxylin absorbs a broad spectrum of light; this phenomenon causes a reduced penetration of illumination light into the tissue, thereby limiting the imaging volume to something slightly thicker than a conventional histology slide. Light that is not absorbed by the hematoxylin is scattered and remitted diffusely. In addition, the illumination light can also induce autofluorescence; both of these processes can generate diffuse illumination appearing to come from "behind" the specimen surface, thus, mimicking the transillumination light in regular bright-field microscopy. Counterstaining with eosin generates the familiar pink-red staining seen in conventional H&E. Together these phenomena create images that are very close to standard histology, and the images can be readily viewed live through a microscope or can be captured using cameras. This technique can be replicated using other stains or stain combinations as well. Moreover, this approach can also be combined with other microscopic modalities for multimodal image capture.

This new technique relies on the absorption and staining properties of specific dyes, such as hematoxylin. When tissue is stained with hematoxylin, white light illumination results in an image that is remarkably "thinner" in terms of imaging volume than images generated with the same illumination but using either fluorescent alternatives to hematoxylin (e.g., Hoechst or DAPI) or other conventional dyes. Theoretically, any dye that has the following properties would be useful to facilitate the reduction of imaging volume: (1) the dye must absorb substantially across the wavelengths being used to illuminate the sample; and (2) the dye must stain an abundance of tissue components to some degree.

However, hematoxylin by itself provides little contrast for non-nuclear tissue components. Accordingly, in histology a second stain is used to provide additional morphological information in a different color. This has traditionally been eosin, which is viewed in brightfield as an absorbing dye that generates a pink color in stained portions of the specimen. When eosin is used in combination with hematoxylin with the proposed technique, an image is obtained that is remarkably close to traditional thin-section histology, both in content and contrast.

In one embodiment, the illumination mechanism for the white dwarf system comprises a white light source and a polarizing beam splitter, wherein only one polarization direction of the white light passes through the beam splitter and reaches the stained sample. Specular reflections from the surface of the sample (or coverslip) carry no color information and should be suppressed. This can be accomplished by collecting the light via the same polarization-maintaining objective and passing it through the polarizing beam splitter. Note that only the perpendicular polarization passes through the beam splitter and reaches the camera to convey absorbance information from the sample. Alternatively, the sample can be illuminated obliquely to prevent specular reflections from entering the objective. In a variation on this oblique illumination technique, we employ ring illumination at the back focal plane of the objective to create angular oblique illumination. This improves the sectioning property of the setup by further decreasing the depth of penetration of the illumination light.

The cross-polarization approach can also be paired with epifluorescence techniques in one or more spectral regions to provide additional information. Such information can arise from: (1) specimen autofluorescence; (2) particular signals arising from additional histology stains, such as propidium iodide to reflect RNA abundance; or (3) from molecular labeling (for example, fluorescently labeled antibodies or the like).

Pathologists are well-versed in interpreting brightfield images. However, outside of special circumstances, they generally do not feel comfortable interpreting relatively unfamiliar fluorescence-mode images. Images acquired using the white dwarf system are intrinsically similar to conventional hematoxylin-and-eosin (H&E)-stained thin section images, which allows for a quick acclimation period. However, because this technique works with thick, fresh or fixed, but unsectioned tissue, it can be performed within minutes of acquiring a tissue specimen. (Steps such as dehydration, paraffin-embedding, sectioning, and mounting on slides are not required, cutting hours off the time needed to acquire high-quality images.) The resulting images can be viewed directly (even by eye through microscope eyepieces), or can be digitally acquired and processed using a variety of tools (either algorithmic or machine-learning-based) to generate images as good as or better than can be visualized on conventional H&E slides.

Other conventional techniques that achieve similar optically sectioned images include: photoacoustic techniques, optical coherence tomography, confocal techniques, multiphoton techniques, light-sheet techniques, structured illumination techniques, and MUSE (microscopy with ultraviolet surface excitation) microscopy. While these techniques have their own pros and cons, they all require conversion to traditional brightfield modalities for interpretation by a pathologist. Moreover, the cost of these systems is considerably more than the cost of the microscopes that are typically deployed in pathology settings, and this cost issue is hindering their widespread adoption.

MUSE is the closest relative to white dwarf. (See A. Qorbani, F. Fereidouni, R. Levenson, S. Y. Lahoubi, Z. T. Harmany, A. Todd, M. A. Fung, Microscopy with ultraviolet surface excitation (MUSE): A novel approach to real-time inexpensive slide-free dermatopathology, J Cutan Pathol, 2018.) Particular differences include the fact that MUSE relies on relatively deep UV excitation (~280 nm) that necessitates the use of non-standard light sources and oblique illumination through UV-transparent sample supports. This general configuration makes it difficult to use high-numerical-aperture, high-magnification lenses that have short working distances, because it is difficult to get objectives close enough to the tissue without blocking the UV excitation light. In addition, the signal strength using available, relatively low-power LEDs requires exposure times in the hundreds of milliseconds versus ~5 ms with white dwarf. Also, the color palette of the acquired MUSE images is not that close to conventional H&E, and some familiar H&E contrast events can be hard to replicate. White dwarf technology uses much brighter conventional light sources and standard epi-collection geometry. These factors allow the use of high-magnification lenses, and imaging times in the low-milliseconds per frame, allowing for much faster large field-of-view imaging. It is also compatible with both fluorescent and absorbing molecular contrast agents, such as are used with immunofluorescence and immunohistochemistry. Moreover, white dwarf provides a non-destructive imaging methodology, which means the imaged tissue is compatible with downstream histology and molecular assays.

Advantages

A white dwarf (WD) system provides a number of advantages: (1) it decreases the present delay from specimen acquisition to diagnostic image viewing from overnight to around three minutes; (2) it can reduce the overall cost of histological processing by at least 50% for conventional histology laboratories; and (3) because of its non-destructive nature and because it allows avoidance of a paraffin-embedding step (and, optionally, of formalin entirely), it can preserve tissue integrity with respect to DNA and RNA quality, which allows for more accurate, higher yield downstream molecular testing.

Because of these advantages, WD has a number of important applications. With WD, the current pathology practice can be extended to deliver high-quality diagnoses in intraoperative settings (currently handled by poor quality and sometimes challenging frozen section-based methods) for major surgical as well as Mohs skin cancer resection procedures. Beyond that, WD can also be used to provide preclinical research support in pharmaceutical and biotechnology settings, for which histology is both time-consuming and expensive.

Also, due to its ability to image fresh tissue with high quality, WD creates a new paradigm for intraoperative guidance by enabling rapid diagnostic or decision-based margin positivity status evaluation. This may be particularly beneficial for breast lumpectomy procedures; because frozen-section-based techniques work poorly with fatty or highly fibrous tissue, it is generally not current practice to evaluate margins in breast tumor resections. In practice, this contributes to a current high rate of re-excisions (as many as 30% of procedures) that are triggered when positive margins are detected following surgery using standard histology.

WD can also significantly improve rapid on-site evaluation (ROSE) for biopsy adequacy, when biopsy specimens are checked to ensure that they contain cells or lesions of interest and in sufficient quantity. Currently, needle biopsy procedures are performed under static or dynamic radiological (or ultrasound) guidance, but accuracy and yield remain problematic. Cytological touch preparation is the method used most widely to assess adequacy, but the associated touch prep sampling and cell-level analysis do not necessarily provide sufficient accuracy. Moreover, a recent study has shown that vigorous touch preparation might cause significant damage to tissue or loss of diagnostic material, which can lead to failure to render a diagnosis and to perform successful downstream molecular testing. WD can also be used to perform histological (intact tissue-level) imaging without harsh sampling, with the potential to not only report adequacy, but to actually deliver diagnostic-grade evaluations. This can be very helpful to patients, who can receive rapid feedback on the results of the procedure rather than waiting days for news on whether the procedure might need to be repeated due to low yield, and more importantly whether or not the biopsy revealed the presence of cancer. Such timely information can also accelerate patient care trajectories.

WD differs from existing cross-polarization imaging techniques for a number of reasons. Polarization imaging is usually performed by illuminating the sample with linear polarized light. As polarized light propagates through tissue, the polarization status of the light changes. Imaging of scattered light in parallel directions blocks the light from deeper layers and facilitates imaging the surface. However, the scattered light from the surface has a large specular reflection or glare, which carries no color information. In some cases, two images are acquired, one in a parallel direction $I_{par}$ and one in a perpendicular direction $I_{per}$, and by calculating $I_{par}-I_{per}$ the glare is removed, and a surface image is created. This approach at the microscopic scale provides an image with poor contrast because it limits the imaging volume to surface layers and provides no useful content. By imaging in cross-polarized mode, the glare is removed, and internal structures can be imaged. This is where the staining with hematoxylin becomes handy. It prevents the light from penetrating deep inside the tissue, and it also ensures that imaging is limited to the surface of the tissue (10 µm), which is slightly deeper than the thickness of regular histology sections (4-6 µm).

Imaging System

Figure 1A:
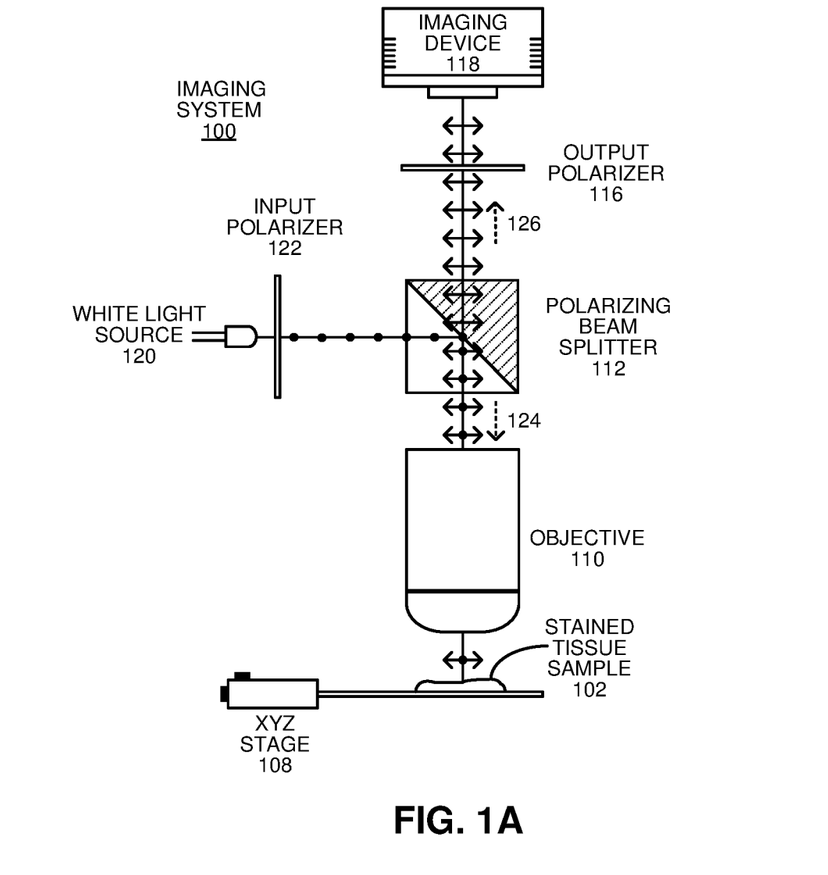
FIG. 1A illustrates a white dwarf imaging system that uses cross polarizers to avoid specular reflection in accordance with the disclosed embodiments.

FIG. 1A illustrates an exemplary white dwarf imaging system 100 in accordance with the disclosed embodiments. As illustrated in FIG. 1A, imaging system 100 includes a sample holder comprising an XZY stage 108, which is configured to hold a stained tissue sample 102. It also includes an objective 110 positioned to gather and focus light from the stained tissue sample 102. Imaging system 100 also includes a white light source 120, which produces unpolarized white light. This white light passes through an optional input polarizer 122 and into a polarizing beam splitter 112. During operation, the polarizing beam splitter 112 first receives white light from the white light source 120. It then allows one polarization direction to pass through to form an illumination beam having a first polarization direction. (Note that the optional input polarizer 122 has a polarization direction, which is substantially the same as the first polarization direction.)

The polarizing beam splitter 112 is also positioned so that the illumination beam 124 is directed through the objective 110 and onto the stained tissue sample 102. This causes the stained tissue sample 102 to remit light, which passes back up through the objective 110 and into the polarizing beam splitter 112. The polarizing beam splitter 112 then divides the remitted light into two orthogonally polarized remitted light beams, wherein one of the polarized remitted light beams provides an imaging beam 126, which has a second polarization direction, which is substantially orthogonal to the first polarization direction. Finally, the imaging beam 126 is directed through an optional output polarizer 116 and into an imaging device 118, which captures the imaging beam 126. Note that the optional output polarizer 116 has a polarization direction, which is the same as the second polarization direction. Also, as mentioned above, the imaging device 118 can include: an eyepiece; a camera; or a digital image-capture device.

Figure 1B:
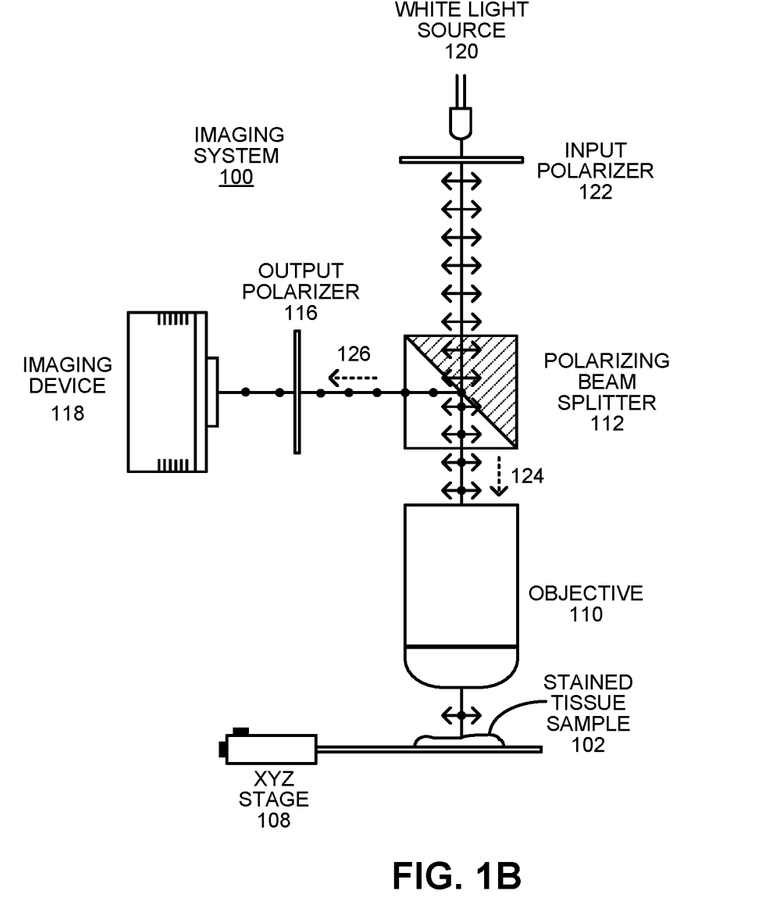
FIG. 1B illustrates a variation of the white dwarf system illustrated in FIG. 1A in accordance with the disclosed embodiments.

FIG. 1B illustrates a variation of the imaging system 100 illustrated in FIG. 1A in which the positions of the white light source 120 and input polarizer 122 in relation to the polarizing beam splitter 112 are swapped with the positions of the imaging device 118 and the output polarizer 116. Otherwise, this variation operates in the same manner as the variation illustrated in FIG. 1A.

Figure 2:
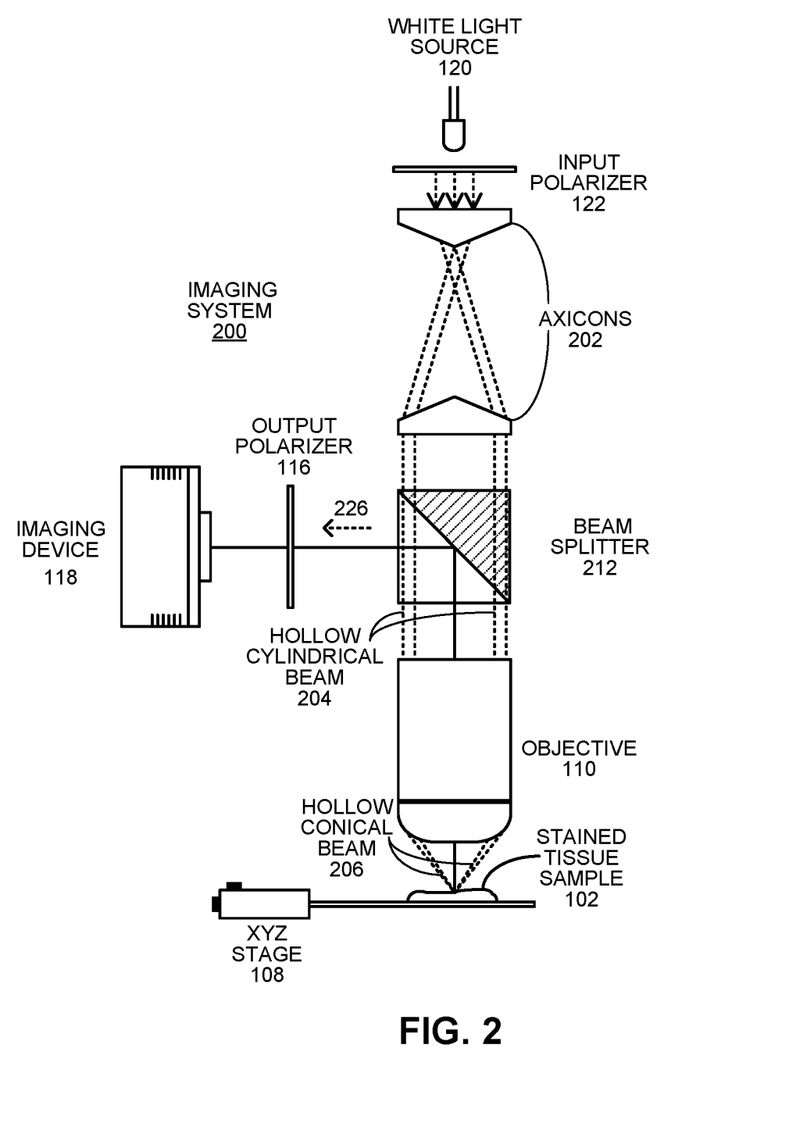
FIG. 2 illustrates an imaging system that provides oblique illumination using conical lens elements called "axicons" in accordance with the disclosed embodiments.

FIG. 2 illustrates a variation of a WD imaging system 200 that provides oblique illumination in accordance with the disclosed embodiments. To provide this oblique illumination, imaging system 200 includes an optical system that directs the unpolarized white light from white light source 120 to the stained tissue sample 102 at an oblique angle relative to an imaging path between the stained tissue sample 102 and an objective 110. As illustrated in FIG. 2, the optical system that provides this oblique illumination can be implemented using a pair of axicons 202, which convert the unpolarized white light into a hollow cylindrical beam 204 that passes through a beam splitter 212 (which can either be an intensity beam splitter or a polarizing beam splitter) and into objective 110. Objective 110 converts the hollow cylindrical beam 204 into hollow conical beam 206, which radially converges on the stained tissue sample 102 to produce oblique illumination. This causes stained tissue sample 102 to remit light that passes back through the objective 110 and into the beam splitter 212. Next, beam splitter 212 reflects a percentage of the remitted light in a perpendicular direction to form an imaging beam 226 that feeds into imaging device 118.

Figure 3:
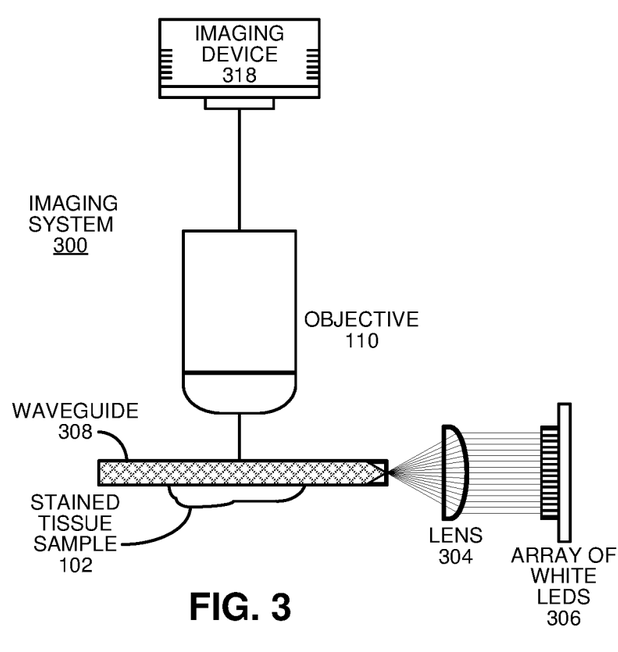
FIG. 3 illustrates an imaging system that illuminates a tissue sample via side illumination from a waveguide in accordance with the disclosed embodiments.

FIG. 3 illustrates another variation of a WD imaging system 300 wherein a stained tissue sample 102 is illuminated via side illumination from a waveguide in accordance with the disclosed embodiments. As illustrated in FIG. 3, imaging system 300 includes a waveguide 308 in the form of a microscope slide coverslip, wherein the stained tissue sample 102 is placed against or in proximity to a surface of the waveguide 308. The illumination source for imaging system 300 comprises an array of white LEDs 306 and a lens 304, wherein the lens 304 focuses light from the array of white LEDs 306 into an input end of the waveguide 308 to provide side illumination. The array of LEDs 306 and the lens 304 are configured so that a launch angle for components of the white light is greater than a critical angle between the waveguide material and air, so that the white light propagates through the waveguide via total internal reflection to reach the stained tissue sample 102. The launch angle is also less than a critical angle between the waveguide material and the stained tissue sample 102, so that when the white light reaches the stained tissue sample, the white light escapes the waveguide 308 through refraction to illuminate the stained tissue sample 102. Imaging system 300 also includes an objective 110 and an imaging device 318, which are located on an opposite side of the waveguide 308 from the stained tissue sample 102.

Figure 4:
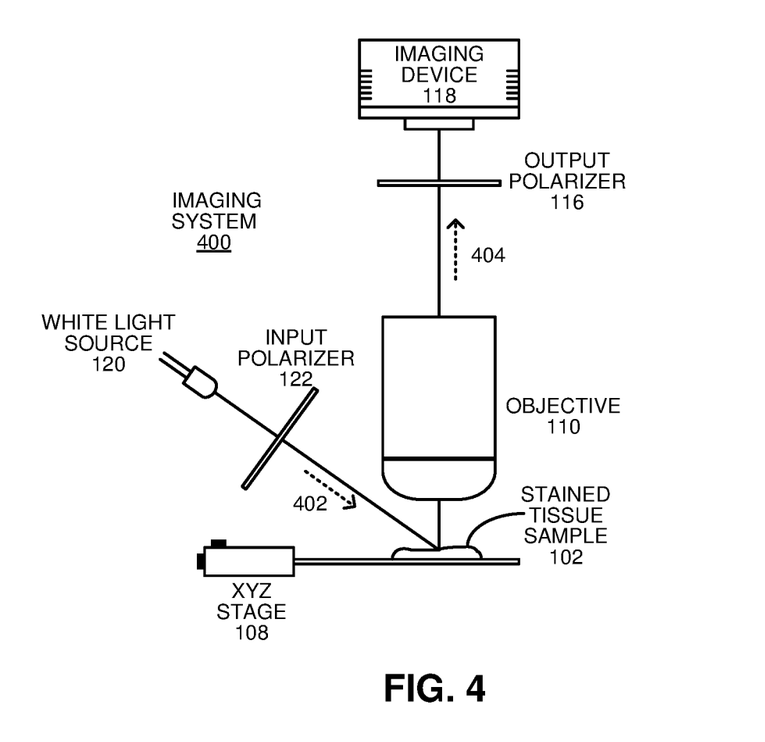
FIG. 4 illustrates an imaging system that provides oblique illumination for a tissue sample in a manner that prevents specular reflection from reaching the imaging device in accordance with the disclosed embodiments.

FIG. 4 illustrates a variation of a WD imaging system 400 that provides oblique illumination of a tissue sample in a manner that prevents specular reflection from reaching the objective in accordance with the disclosed embodiments. In this variation, a white light source 120 and an input polarizer 122 produce an illumination beam 402 comprising polarized white light, which hits the stained tissue sample 102 at an oblique angle relative to an imaging path between the stained tissue sample 102 and an objective 110 to produce oblique illumination. This oblique illumination causes the stained tissue sample 102 to remit light with greatly reduced specular reflection components. The remitted light passes through the objective 110 to form an imaging beam 404 that feeds through an optional output polarizer 116 into imaging device 118.

Imaging Process

Figure 5:
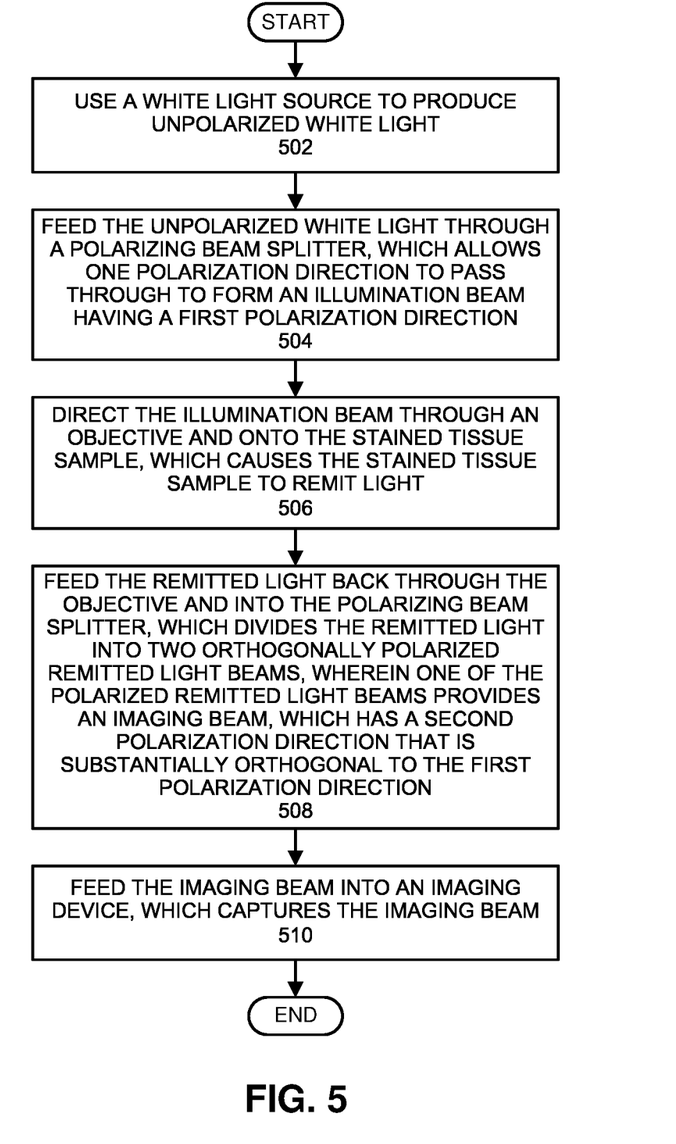
FIG. 5 presents a flow chart illustrating a process for imaging a tissue sample in accordance with the disclosed embodiments.

FIG. 5 presents a flow chart illustrating a process for imaging a tissue sample in accordance with the disclosed embodiments. During operation, the system uses a white light source to produce unpolarized white light (step 502). Next, the system feeds the unpolarized white light through a polarizing beam splitter, which allows one polarization direction to pass through to form an illumination beam having a first polarization direction (step 504). Next, the system directs the illumination beam through an objective and onto the stained tissue sample, which causes the stained tissue sample to remit light (step 506). The system feeds the remitted light back through the objective and into the polarizing beam splitter, which divides the remitted light into two orthogonally polarized remitted light beams, wherein one of the polarized remitted light beams provides an imaging beam, which has a second polarization direction that is substantially orthogonal to the first polarization direction (step 508). Finally, the system feeds the imaging beam into an imaging device, which captures the imaging beam (step 510).

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A system for imaging tissue, comprising:
tissue having a surface stained with one or more absorbing stains;
a light source that produces unpolarized light;
a first polarizer that receives the unpolarized light and forms an illumination beam having a first polarization state that transits the stained surface and that, after experiencing multiple scatter events below the stained surface, and resultant depolarization, forms diffuse illumination below the stained surface;
an objective that collects a signal comprising a portion of the diffuse illumination that is remitted through the stained surface and that contains tissue details from the stained surface only; and
a second polarizer that forms illumination having a second polarization state substantially orthogonal to the first polarization state, wherein the second polarizer substantially blocks specular reflections from the surface of the tissue and transmits the signal to an imaging device.

2. The system of claim 1, wherein the imaging device includes one of the following:
an eyepiece;
a camera; and
a digital image-capture device.

3. The system of claim 1, wherein the stained tissue is not sectioned.

4. The system of claim 1, wherein the stained tissue is stained with hematoxylin.

5. The system of claim 1, wherein the stained tissue is stained with one or more of the following absorbing stains: eosin, rhodamine, saffron, and celestine blue.

6. The system of claim 1, further comprising a sample holder positioned using an XYZ stage.

7. The system of claim 1, wherein the system is combined with an epifluorescence microscopy system to provide additional information in resulting images.

8. The system of claim 1, wherein digital images that are captured by the imaging device are computationally processed to facilitate one or more of the following: image enhancement, denoising, computational superresolution, color-mapping and machine-learning based image-processing.

9. The system of claim 1, wherein:
the imaging device yields a real-time diagnostic-quality image of the tissue details from the signal.

10. The system of claim 1, wherein:
the objective limits image acquisition to no more than 10 µm below the surface.

11. A system for imaging a tissue sample, comprising:
a sample holder configured to hold a tissue sample having a surface stained with an absorbing stain;
an objective positioned to gather and focus light remitted from the surface of the stained tissue sample;
a white light source that produces unpolarized white light;
an optical system that directs the unpolarized white light to the surface of the stained tissue sample at an angle relative to an orthogonal imaging path between the surface of the stained tissue sample and the objective to produce non-orthogonal illumination, wherein the non-orthogonal illumination transits the surface to form diffuse illumination below the surface that remits through the surface through the objective to form an imaging beam containing tissue details from only the surface, wherein the optical system blocks specular reflections from the surface of the tissue sample, and wherein the imaging beam comprises only polarized remitted light; and an imaging device positioned to receive the imaging beam.

12. The system of claim 11, wherein the optical system comprises:

a beam splitter; and a pair of axicons, which convert the unpolarized white light into a hollow cylindrical beam that passes through the beam splitter and into the objective, wherein the objective converts the hollow cylindrical beam into a hollow conical beam, which radially converges on the stained tissue sample to produce the non-orthogonal illumination, which causes the surface of the stained tissue sample to remit the light that passes through the objective and into the beam splitter;

wherein the beam splitter reflects a percentage of the remitted light in a perpendicular direction toward the imaging device.

13. The system of claim 11, further comprising an input polarizer located between the white light source and the optical system, wherein the input polarizer has a first polarization state.

14. The system of claim 13, further comprising an output polarizer located between the optical system and the imaging device, wherein the output polarizer has a second polarization state that is substantially orthogonal to the first polarization state.

15. The system of claim 11, wherein the imaging device includes one of the following:

an eyepiece;

a camera; and a digital image-capture device.

16. The system of claim 11, wherein the stained tissue sample is thick and unsectioned.

17. The system of claim 11, wherein the stained tissue sample is stained with hematoxylin.

18. The system of claim 17, wherein the stained tissue is stained with one or more of the following absorbing stains: eosin, rhodamine, saffron, and celestine blue.

19. The system of claim 11, wherein the sample holder is positioned using an XYZ stage.

20. A method of imaging stained tissue, the method comprising:

staining a tissue surface with one or more absorbing stains;

energizing a light source to produce unpolarized light;

polarizing the unpolarized light to yield an illumination beam polarized in only a first state, for transiting the stained tissue surface to produce diffuse illumination below the tissue surface, a portion of which remits through the tissue surface and contains details from only the tissue surface;

receiving unpolarized light remitted from the stained tissue surface;

filtering the unpolarized remitted light to yield an imaging beam polarized in only a second state, wherein said filtering substantially blocks specular reflections from the stained tissue surface; and at an imaging device, receiving the imaging beam and producing an image of the stained tissue surface in real-time.

21. The method of claim 20, wherein acquisition of the image is limited to a depth of no more than 10 μm from the tissue surface of the stained tissue.

22. The method of claim 20, wherein the stained tissue is thick and unsectioned.

* * * * *